(12) United States Patent
Goetheer et al.

(10) Patent No.: US 8,298,396 B2
(45) Date of Patent: Oct. 30, 2012

(54) PROCESS AND APPARATUS FOR THE PRODUCTION AND SEPARATION OF FERMENTATION PRODUCTS

(75) Inventors: Earl Lawrence Vincent Goetheer, Westdorpe (NL); Joost van Erkel, Apeldoorn (NL); Koen Peter Henri Meesters, Amersfoort (NL); Roel Johannes Martinus Bisselink, Zeddam (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 1294 days.

(21) Appl. No.: 11/661,059

(22) PCT Filed: Sep. 2, 2005

(86) PCT No.: PCT/NL2005/000635
§ 371 (c)(1),
(2), (4) Date: Aug. 22, 2007

(87) PCT Pub. No.: WO2006/025740
PCT Pub. Date: Mar. 9, 2006

(65) Prior Publication Data
US 2008/0060948 A1     Mar. 13, 2008

(30) Foreign Application Priority Data

Sep. 3, 2004   (EP) ..................... 04077466

(51) Int. Cl.
*B01D 43/00*   (2006.01)
*C25B 7/00*    (2006.01)
*C12P 7/40*    (2006.01)
*C12P 13/04*   (2006.01)

(52) U.S. Cl. ......... 205/688; 205/687; 435/106; 435/136
(58) Field of Classification Search .......... 204/280, 204/282, 541, 544, 629, 630, 649, 650; 205/687, 205/688, 703; 435/108, 110, 115, 136, 142, 144, 145, 146
See application file for complete search history.

(56) References Cited

U.S. PATENT DOCUMENTS

| | | | | |
|---|---|---|---|---|
| 2,216,167 | A | * | 10/1940 | Fisher ........................... 205/74 |
| 5,106,468 | A | * | 4/1992 | Chimenti ..................... 204/564 |
| 5,681,728 | A | * | 10/1997 | Miao ............................. 204/527 |
| 6,312,582 | B1 | * | 11/2001 | Thauront et al. .............. 205/440 |

FOREIGN PATENT DOCUMENTS

| | | |
|---|---|---|
| EP | 1 415 702 A | 5/2004 |
| JP | 63 188385 A | 8/1988 |
| WO | WO 2004/046351 | 6/2004 |

OTHER PUBLICATIONS

Li et al., "An Electrokinetic Bioreactor: Using Direct Electric Current for Enhanced Lactic Acid Fermentation and Product Recovery", *Tetrahedron, Elsevier Science Publishers*, vol. 60:3; pp. 655-661; Jan. 2004.

Mustachhi et al., "Enhanced Biotransformations and Product Recovery in a Membrane Bioreactor Through Application of a Direct Electric Current", *Biotechnology and Bioengineering*, vol. 89:1; pp. 18-23; Jan. 2005.

* cited by examiner

*Primary Examiner* — Keith Hendricks
*Assistant Examiner* — Steven A. Friday
(74) *Attorney, Agent, or Firm* — Hoffmann & Baron, LLP

(57) ABSTRACT

The invention is directed to processes and apparatuses for the production of chemical compounds, in particular fermentation products. According to the invention there is provided a process for the production of one or more chemical substances, which process comprises a fermentation step, wherein said substances are formed; and a separation step, wherein at least one pair of electrodes is used to induce a precipitation of said substances, which pair comprises at least one precipitation electrode and at least one counter electrode, through which an electric current is directed is used to precipitate said one or more substances.

17 Claims, No Drawings

PROCESS AND APPARATUS FOR THE
PRODUCTION AND SEPARATION OF
FERMENTATION PRODUCTS

This application is the U.S. National Phase of, and Applicants claim priority from, International Application Number PCT/NL2005/000635 filed 2 Sep. 2005 and European Patent Application bearing Serial No. EP 04077466.3 filed 3 Sep. 2004, which are incorporated herein by reference.

BACKGROUND OF THE INVENTION

The invention is directed to processes and apparatuses for the production of chemical compounds, in particular fermentation products.

Fermentation processes are commonly employed for the preparation of chemical compounds, such as amino acids or carboxylic acids. In practice, it is usually difficult to operate such processes in an economically feasible way, because the costs of separating the fermentation products can be quite high. These high costs are caused on the one hand by the relative low concentration in which the compounds are produced, and on the other hand by the complex nature of the fermentation medium (the broth). Separation of the chemical species produced by the fermentation reactions is at present commonly achieved by one or more steps of removal of non-desired compounds from the broth, followed eventually by isolation of the desired product. In particular when organic acids are produced, after an optional concentration step, it is common practice to facilitate the separation of these acids by the addition of acids. These known procedures are inefficient and together often give rise to large amounts of waste, such as certain salts (gypsum, sodium sulphate, ammonium sulphate), organic solvents, adsorption particles, etc.

At the same time, the possibilities for producing chemical compounds via a biotechnological route are ever increasing, in particular as a result of the increased possibilities for genetic modification of micro-organisms. One of the problems that frequently occur when chemical species are produced by micro-organisms is that the production rate is suppressed after some time as a result of product inhibition (e.g. because the products are toxic in a high concentration and/or because of the equilibrium reactions involved). Also for instance in the case of production of organic acids, the pH of the broth shifts towards values below the optimal production range. To reach as high as possible product concentrations, in common practice, alkaline chemicals are added to the broth during the fermentation process. This not only results in an increase of the osmotic pressure (which is harmful for the fermentation species), but again also leads to large amounts of waste such as gypsum, ammonium sulphate, and/or sodium sulphate.

A process used for separating products from a fermentation process is electrodialysis fermentation. This process is known from e.g. Li et al. *Tetrahedron* 2004, 60, 655-661; WO-A-2004/046351; JP-A-63 188385; and EP-A-1 415 702. Electrodialysis is a membrane separation process for dissolved ionic species based on the transfer of ions through selective membranes under the influence of an electric field. In electrolysis process operations the formation of precipitates is highly unwanted because precipitation leads to a blocking of the membrane pores and thus disturbs the free migration of species. Electrodialysis processes thus produce a solution of the dissolved product(s) from which the product itself has to be isolated by conventional chemical separation techniques.

It would thus be highly desirable to develop techniques that are capable of removing fermentation products from the fermentor, preferably in-situ, thus without interfering (or with only very minimal interference) to the fermentation process itself. In addition, it would be desirable if such techniques can be employed relatively easily on existing fermentation facilities (retrofitting), without requiring much adaptation to the equipment. Furthermore, the present invention aims in particular at the production by fermentation and subsequent separation of carboxylic acids and amino acids, which compounds have been notoriously difficult to separate from the fermentation broth in the past.

DESCRIPTION OF THE INVENTION

It has been found that the above-mentioned objectives can be met by locally changing the pH of the fermentation broth by using one or more electrodes, thereby exceeding the solubility of the product and inducing precipitation. Thus the present invention is directed to a process for the production of one or more chemical substances, which process comprises a fermentation step, wherein said substances are formed; and a separation step, wherein at least one electrode pair is used to induce a precipitation of said substances, through which an electric current is directed is used to precipitate said one or more substances.

The fermentation medium of fermentation processes generally has a pH in the range of about 5 to about 9. For the precipitation of organic acids, such as e.g. cinnamic acid, this is too high, since the majority of the cinnamic acid will be present as its salt (e.g. sodium cinnamate), which has a solubility that is much higher than cinnamic acid. Thus it is difficult to separate the product at these high pH values and lowering of the pH is necessary. Addition of acids, for in situ product recovery, as discussed hereinabove, is not desirable, since lowering of the pH of the fermentation medium decreases the activity of the micro-organisms and thus decreases the production rate. The same applies for other products than cinnamic acid.

By applying the electrodes in accordance with the present invention, acidic (protons) or basic (OH—) species can be produced near the electrodes and the pH can thus be controlled locally, viz. without disturbing the rest of the fermentation medium. By controlling the pH, the solubility of the products (in particular organic acids and amino acids) can be lowered locally, which results in deposition of these compounds on the electrodes, or in the near vicinity of the electrodes, in particular within the diffusion layer directly adjacent to the electrodes. The diffusion layer in this context is meant to be the layer at the electrode in which mass transport is dominated by diffusion, this in contrast to the bulk in which mass transport occurs mainly through convection. The diffusion layer thickness $\delta$ may be defined by:

$$\delta = \frac{D}{k_d}$$

wherein D is the diffusion constant, and $k_d$ is the heterogeneous diffusion rate constant. Typical values for D lie around $10^{-9}$ m²/s (e.g. $10^{-10}$-$10^{-8}$ m²/s), and for $k_d$ typically in the range of $10^{-4}$-$10^{-7}$ m/s. The diffusion layer thickness therefore typically lies in the range of $10^{-5}$ to $10^{-2}$ m, in particular from 0.01 to 1 mm, e.g. about 0.5 mm.

Precipitation outside the diffusion layer generally does not occur in accordance with the present invention, because this normally only occurs if the pH of the bulk is lower than the pK$_a$. Such pH values, however, are typically not in the pH range of the fermentation medium for fermentation processes of the present invention.

The product may then be obtained as a deposition on the electrodes, as flakes (or flocks) in the medium and/or as froth that will float to the top of the medium.

The electrode can be placed in the compartment wherein the fermentation is carried out, viz. in the fermentor itself, so that in situ product removal is obtained. In that case the product formed must be removed by vibrating, or scraping the electrodes (if it is formed thereon), applying periodic mechanical shocks to the electrode that contains the precipitate, skimming the broth (in particular if a froth is formed) and/or filter means to remove the flocks (if these are formed within the fermentation medium), whichever is most appropriate.

It is of course also possible and within the scope of the present invention to contact the fermentation broth (including the product) with the electrodes, outside the fermentor, e.g. by taking a small stream of broth and contacting it with the electrodes in a separate compartment and subsequently recycling the stream that is obtained by removing the product back to the fermentor. Again, the product formed must be removed by vibrating or scraping the electrodes, applying mechanical shocks, reversal of the electrode potentials, skimming the broth and/or filter means to remove the flocks, whichever is most appropriate.

It is important that while the separation is carried out, the electrodes are applied such that an electric current can flow through the medium. Thus, there should be at least two electrodes, one anode that is in electric contact with at least one cathode. The electric contact should be provided by the fermentation medium, optionally via a separator and complementary electrolyte solution for the counter electrode.

The product that is deposited on the electrodes (e.g. by crystallization) can be removed by scraping the electrodes. To facilitate this process, the electrodes can be provided e.g. as rotating electrodes or as dipping electrodes. The scraping of electrodes is known per se (e.g. from the electrochemical metal production, refining, and recycling industries) and can be carried out using e.g. plastic scraping devices. Thus, in one embodiment, the electrode on which the product is deposited is removed from the medium, e.g. in a constant cycle by using rotating electrodes so that simultaneously a fresh (clean) electrode is submerged, and removing the product from the covered electrode by scraping and collecting.

Typically, a pair of electrodes is used; one anode and one cathode, which are placed at a predetermined distance from each other, e.g. in the fermentation vessel. Subsequently a suitable voltage is applied (typically from 2-20 V, more preferably 3 to 15 V, e.g. about 5 V) which results in an electric current (e.g. having a current density of typically 100-10 000 A/m$^2$, preferably about 500 to 5000 A/m$^2$) and electrolysis is allowed to take place. The following electrochemical reactions may occur.

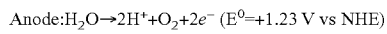

Anode: $H_2O \rightarrow 2H^+ + O_2 + 2e^-$ ($E^0 = +1.23$ V vs NHE)

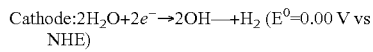

Cathode: $2H_2O + 2e^- \rightarrow 2OH^- + H_2$ ($E^0 = 0.00$ V vs NHE)

The water concentration at the electrodes is not significantly affected by the conversion of water molecules, and has a constant value throughout the solution. However, the concentration of the protons, which are formed from the water molecules, has the highest value at the place where these protons are produced, viz. at the anode surface; this proton concentration is controlled by the applied current density. The produced protons then diffuse towards the bulk of the solution through the stagnant (diffusion) layer at the anode. Consequently, a proton concentration gradient is formed in this diffusion layer. At the start of the electrolysis reaction the concentration of organic anions (e.g. cinnamate ions) is the same, irrespective of the location in the solution. After the start of the electrolysis, organic anions (e.g. cinnamate ions) will react with protons to form the corresponding acid (e.g. cinnamic acid). Since the proton concentration has the highest value in the diffusion layer at the anode, the maximum solubility of the organic acid will be obtained there first, and consequently the acid will deposit (e.g. by crystallization) on the anode, and/or in the diffusion layer at the anode.

The same mechanism applies mutatis mutandis for the OH— ions produced at the cathode, which may be used to deposit basic substances and amino acids. The solubility of amino acids goes through a minimum value at (or around) their individual iso-electric point. Thus, if the broth has a pH-value above the iso-electric point of a certain amino acid, the H$^+$ ions produced at the anode will cause the precipitation. Whereas, if the fermentation broth has a pH-value below the amino acid's iso-electric point, the OH— produced at the cathode will bring about the precipitation. Thus, in a preferred process according to the present invention the product substance is selected from organic acids, amino acids and combinations thereof.

In a preferred embodiment according to the present invention, the electric current is reversed (by reversing the + and the − of the electric power supply, for instance using an arrangement of electric switches) for a certain period of time (e.g. 1-300 seconds), which results in redissolving the product and which is a convenient means to remove the product from the electrodes. This facilitates removal of the product from the electrode considerably.

To improve the conductivity of the medium, it is preferred to dissolve an electrolyte (e.g. Na$_2$SO$_4$, NaClO$_4$, etc.) therein.

Preferably the organic acids are selected from the group consisting of citric acid, cinnamic acid, hydroxycinnamic acid, succinic acid, adipic acid, p-hydroxybenzoic acid, and combinations thereof. In another preferred embodiment, the compounds produced are amino acids, more preferably amino acids selected from the group consisting of glutamic acid, lysine, phenylalanine, and combinations thereof. Also combinations of the compounds mentioned can be produced according to the present invention.

When the electrode is an anode, it preferably comprises one or more of:

- titanium, more preferably titanium that is coated with noble metal oxides (in particular IrOx, RuOx, TaOx, or mixtures thereof), also known as dimension stable anodes (DSA);
- graphite or carbon;
- diamond coated electrodes (including Boron Doped Diamond electrodes);
- Ni, V, Cr, Fe—alloys (HASTELLOY™, INCONEL™, and the like);
- Spinels of Ni/Co; and
- Oxides of Pb alloys.

Suitable cathode materials comprise one or more of:
- iron;
- steel;
- nickel;
- nickel alloys (nickel-molybdenum, nickel-cobalt, nickel-chromium, and the like);
- noble metals (Pt, etc.);
- alloys of noble metals; and
- graphite and/or carbon.

The electrodes may have any suitable shape and dimension. Preferred shapes are plates, rods, discs, gauzes, foames, or a packed bed of particles. Typical dimensions depend on the size of the equipment used, in particular of the fermentation vessel employed, but generally the surface of the electrode may be in the range of 0.5 to 50 m² or more.

Thus, in one embodiment, the present invention is directed to a process, wherein the chemical substance, which is the product of the fermentation step, is recovered in situ, viz. in the fermentation broth. To this end, the electrode which induces the product precipitation is placed in the fermentation broth. The counter-electrode may be placed in an adjacent compartment. The adjacent compartment can be a different vessel or it may be a part from the fermentor that is separated by suitable means, such as a glass frit or a membrane. The fermentation compartment and the adjacent compartment should be in electrical contact with each other. Instead of in an adjacent compartment, it is also possible to place the counter-electrode in the same compartment, viz. in direct contact with the fermentation broth. The advantage of having both types of electrodes in the same compartment is that when organic acids are produced by the fermentation step, the cathode produces OH—, in an amount that is equivalent with the amount of acid that is removed by crystallization/precipitation on the anode. This means that the addition of pH-regulating chemicals can be avoided. The current density in this embodiment is preferably adjusted such that it keeps track with the production rate of the micro-organisms. The advantages of this embodiment are that the conditions in the fermentor are kept (substantially) constant, viz. the osmotic pressure remains substantially the same, there is substantially no product inhibition, since the concentration of the product remains substantially the same, etc. Thus the fermentor can be operated for a longer time without the need for interference in the fermentation process. Also there is a cost advantage, since no chemicals are required for pH regulation and the production of waste (gypsum, etc.) is avoided.

It is also possible to recover the product from the fermentation medium by circulating a small stream outside the fermentor and contacting this small stream with the electrodes. After the product is precipitated and (thus) removed from the medium, the remainder of the fluid can be returned to the fermentor.

The invention will now be illustrated by the following non-limiting examples.

EXAMPLES

Equipment and Conditions

The electrolysis reactor that was used had separate compartments for the anolyte and catholyte. The volumes of the anolyte and the catholyte were ca. 1 dm.sup.3 each. The compartments were separated from each other by cation exchanging membrane (type NAFION™ N424). Platinum gauze having a total surface of 40 cm² was used as an anode. A scraper made from a polymeric material was used to scrape the surface of the anode. A stainless steel plate was used as the cathode. The anode and the cathode were connected to a DC power supply (Delta Elektronika Power Supply E060-6), which was used as a galvanostate (viz. it provided a constant direct current). Temperature (using a PT100 resistant), electric current, the anode- and cathode potential, the cell voltages and the potential drop across the membrane were measured using multimeters (METRA 23S). The differential potential measurements were carried out using saturated calomel-electrodes (SCE type Radiometer REF401). Anolyte and catholyte were stirred with a IKA RW20 top stirrers. The pH values in anolyte and catholyte were measured using combined glass electrodes (type Radiometer CL116RP; XC250) connected to Schott Gerate pH-meter CG817T. The conductivity was measured using a Radiometer CDC364 cell, which was connected to a Radiometer Copenhagen CDM83 conductivity meter.

The following examples were carried out.

Example 1

Reference, not in Accordance with the Invention

The anode compartment was filled with 0.750 dm³ 0.25 M sodium cinnamate solution (0.19 mol cinnamate). The conductivity of the solution was 13.1 mS/cm; and the pH 6.0; the temperature was 23° C. The cathode compartment was filled with 780 ml 0.1 M $NaClO_4$ (18.6 mS/cm). The current was adjusted to I=1 A, which corresponds to a current density, J, of 25 mA/cm².

Example 2

Reference, not in Accordance with the Invention

The anolyte was 0.900 dm³ solution with 0.25 M sodium cinnamate (0.225 mol) and 0.5 M $Na_2SO_4$. The conductivity was 59 mS/cm. The pH was 8.0. The temperature was 22° C. 1.0 liter 0.5 M $Na_2SO_4$ solution was used as catholyte. The current density was again adjusted to I=1 A, which corresponds to a current density, J, of 25 mA/cm2.

Example 3

Inventive Example

The anolyte was 0.980 liter 0.09 M sodium cinnamate (0.088 mol), 0.18 M $Na_2SO_4$ and fermentation liquid *Pseudomonas putida* S12. The conductivity was 33.7 mS/cm, the pH 7.1, and the temperature 23° C. The catholyte of Example 2 was reused. During 1 hour the current density, J, was 25 mA/cm² (I=1 A), after which a value of J=100 mA/cm² (I=4 A) was used.

Results

Example 1

The pH value of the bulk of the anolyte was at pH~6.0 ($pH_{t=0}$=6.0; $pH_{t=1h}$=5.8), which resulted in the cinnamate ion being the dominant species in the bulk of the solution, rather than cinnamic acid.

Under these conditions, solid cinnamic acid was deposited on the anode. Scraping of the anode produced white flocks that were dispersed into the stirred solution. After 1 hour the experiment was stopped. The temperature of the anolyte had risen to 39.6° C. The conductivity of the anolyte was 20.5 mS/cm. The anode was covered with solid cinnamic acid, that formed a solid, hard, white deposition, which dissolved slowly 0.5 M NaOH solution and which dissolved fast in ethanol. After 1 hour of electrolysis, the pH in the catholyte was 11.3 and the conductivity was 44.2 mS/cm. There was no precipitation of solid material observed in the cathode compartment. Also the membrane was clean.

Example 2

The pH of the anolyte decreased after 1 hour electrolysis from pH=8.0 to pH=6.2. Thus the cinnamate ion was again the dominant species in the bulk of the anolyte solution. Directly after starting the experiment, a white deposition of cinnamic acid was observed on the anode. After about 10 minutes of electrolysis the presence of cinnamic acid was observed as small flocks in the anolyte. After 15 minutes of electrolysis the anode was scraped and it was observed that the number of flocks had dramatically increased. After 30 minutes of electrolysis, and after scraping the anode for a second time, a very large number of flocks was observed. Subsequently, the stirring intensity was increased. In the second half hour of electrolysis, a white, airy foam (froth) was formed on the anolyte. The temperature of the anolyte did not exceed 23° C. The conductivity of the anolyte was 60 mS/cm. During the experiment the anode voltage was $E_A$=+2.6 V (vs SCE). The potential drop across the membrane was 1.0 V. After 1 hour of electrolysis the pH of the catholyte was 12.4 and the conductivity was 68 mS/cm.

The cinnamic acid deposited at to the anode. The membrane was again free of any depositions.

Example 3

The pH of the anolyte decreased in the first hour of electrolysis from pH=7.1 to pH=5.6. Thus the cinnamate ion was again the dominant species. Directly after starting the experiment, a white deposition of cinnamic acid was observed on the anode. The solution was vigorously stirred. The cinnamic acid did not attach to the electrode but formed a foam. After 1 hour the anolyte was coloured intensely white by the amount of precipitated cinnamic acid and foam. The conductivity of the anolyte was 32.6 mS/cm. The anode potential, $E_A$ was +3.2 V (vs SCE). The potential drop across the membrane was 1.3 V.

The experiment was continued with a current density of 100 mA/cm$^2$.

After 90 minutes of electrolysis the experiment was stopped. The pH of the anolyte and the catholyte was 4.6 and 12.7, respectively. The conductivity of the anolyte was decreased strongly to 16.5 mS/cm. Again the deposited cinnamic acid was not attached to the anode, but formed a layer of cinnamic acid on the anolyte, that could easily be removed therefrom. The membrane was again clean and free of any deposited material.

The invention claimed is:

1. Process for the production of one or more chemical substances, which process comprises:
   a fermentation step of a fermentation broth, wherein said one or more chemical substances are formed; and
   a separation step, wherein a pair of electrodes contacts said fermentation broth and is used to locally change the pH of the fermentation broth, thereby exceeding the solubility of said one or more chemical substances and inducing precipitation of said one or more chemical substances, which pair comprises at least one precipitation electrode and at least one counter electrode, through which electrodes an electric current having a current density is directed, whereby said one or more chemical substances precipitates on, or within the diffusion layer directly adjacent to, said precipitation electrode, wherein said one or more chemical substances are selected from:
   organic acids selected from the group consisting of citric acid, cinnamic acid, hydroxycinnamic acid, succinic acid, adipic acid, p-hydroxybenzoic acid, and combinations thereof;
   amino acids selected from the group consisting of glutamic acid, lysine, phenylalanine, and combinations thereof; and
   combinations thereof.

2. Process according to claim 1, wherein said precipitation of said one or more chemical substances occurs within the diffusion layer directly adjacent to said precipitation electrode.

3. Process according to claim 1, wherein one precipitation electrode is placed in a compartment wherein the fermentation is carried out.

4. Process according to claim 1, wherein said precipitation electrode is an anode to precipitate acidic compounds.

5. Process according to claim 1, wherein both the precipitation electrode and the counter electrode are placed in a fermentation vessel.

6. Process according to claim 5, wherein an organic acid is precipitated on an anode and wherein the current density is adjusted such that the production rate of organic acid salts in said fermentation step is substantially the same as the rate at which said organic acid is precipitated at said anode.

7. Process according to claim 1, wherein said one or more chemical substances are selected from organic acids.

8. Process according to claim 1, wherein one of said pair of electrodes is an anode that comprises one or more of titanium; graphite or carbon; diamond coated electrodes; alloys which include Ni, V, Cr, or Fe; spinels of Ni/Co; and oxides of Pb alloys.

9. Process according to claim 1, wherein one of said pair of electrodes is a cathode that comprises one or more of iron; steel; nickel; nickel alloys; noble metals; alloys of noble metals; and graphite and/or carbon.

10. Process according to claim 1, wherein said electric current has a density of 100-10 000 A/m$^2$, and the cell voltage is 2-20 V.

11. Process according to claim 1, wherein said one or more chemical substances are formed on at least one electrode and the electric current is reversed prior to removal of the one or more chemical substances from said at least one electrode.

12. Process according to claim 1, wherein the one or more chemical substances is/are removed by flotation and/or skimming.

13. Process according to claim 8, wherein said titanium is coated with a noble metal oxide.

14. Process according to claim 13, wherein said noble metal oxide is IrOx, RuOx, TaOx, or mixtures thereof.

15. Process according to claim 13, wherein said diamond coated electrode is a boron doped diamond electrode.

16. Process according to claim 9, wherein said nickel alloy is nickel-molybdenum, nickel-cobalt, or nickel-chromium.

17. Process according to claim 9, wherein said noble metal is platinum.

* * * * *